(12) United States Patent
Zasypkin

(10) Patent No.: US 9,119,411 B2
(45) Date of Patent: *Sep. 1, 2015

(54) MELT EXTRUSION ENCAPSULATION OF FLAVORS AND OTHER ENCAPSULATES IN A CARRIER CONTAINING SPICES AND HERBS

(75) Inventor: Dmitriy Zasypkin, Cockeysville, MD (US)

(73) Assignee: McCormick & Company, Incorporated, Sparks, MD (US)

(*) Notice: Subject to any disclaimer, the term of this patent is extended or adjusted under 35 U.S.C. 154(b) by 75 days.

This patent is subject to a terminal disclaimer.

(21) Appl. No.: 13/087,732

(22) Filed: Apr. 15, 2011

(65) Prior Publication Data

US 2011/0256199 A1 Oct. 20, 2011

Related U.S. Application Data

(60) Provisional application No. 61/325,099, filed on Apr. 16, 2010.

(51) Int. Cl.
| | |
|---|---|
| *A01N 25/08* | (2006.01) |
| *A23L 1/00* | (2006.01) |
| *A23L 1/22* | (2006.01) |
| *A23P 1/04* | (2006.01) |
| *A23P 1/12* | (2006.01) |
| *A61K 9/16* | (2006.01) |

(52) U.S. Cl.
CPC .............. *A23L 1/0076* (2013.01); *A23L 1/0029* (2013.01); *A23L 1/22016* (2013.01); *A23P 1/04* (2013.01); *A23P 1/12* (2013.01); *A61K 9/1652* (2013.01)

(58) Field of Classification Search
None
See application file for complete search history.

(56) References Cited

U.S. PATENT DOCUMENTS

| | | | |
|---|---|---|---|
| 2,809,895 A | 10/1957 | Swisher | |
| 2,856,291 A | 10/1958 | Schultz | |
| 3,314,803 A | 4/1967 | Dame, Jr. et al. | |
| 3,704,137 A | 11/1972 | Beck | |
| 3,971,852 A | 7/1976 | Brenner et al. | |
| 4,230,687 A | 10/1980 | Sair et al. | |
| 4,232,047 A * | 11/1980 | Sair et al. | ............ 426/96 |
| 4,532,145 A | 7/1985 | Saleeb et al. | |
| 4,689,235 A | 8/1987 | Barnes et al. | |
| 4,707,367 A | 11/1987 | Miller et al. | |
| 4,816,298 A | 3/1989 | Alderman et al. | |
| 5,009,900 A | 4/1991 | Levine et al. | |
| 5,087,461 A | 2/1992 | Levine et al. | |
| 5,124,162 A | 6/1992 | Boskovic et al. | |
| 5,603,971 A | 2/1997 | Porzio et al. | |
| 5,756,136 A | 5/1998 | Black et al. | |
| 5,897,897 A * | 4/1999 | Porzio et al. | ............ 426/96 |
| 5,972,395 A | 10/1999 | Saleeb et al. | |
| 6,174,514 B1 * | 1/2001 | Cherukuri et al. | ............ 424/48 |
| 6,187,351 B1 | 2/2001 | Porzio et al. | |
| 6,416,799 B1 | 7/2002 | Porzio et al. | |
| 6,652,895 B2 | 11/2003 | Porzio et al. | |
| 6,790,453 B2 * | 9/2004 | Porzio et al. | ............ 424/408 |
| 6,932,982 B2 | 8/2005 | McIver et al. | |
| 2010/0289164 A1 | 11/2010 | Porzio et al. | |

OTHER PUBLICATIONS

U.S. Appl. No. 13/828,533, filed Mar. 14, 2013, Zasypkin, et al.
H. Levine and L. Slade, "Glass Transitions in Foods", in *Physical Chemistry of Foods*, H. Schwartzberg and R. Hartel, Eds., Marcel Dekker, New York, pp. 83-221, 1992.
H. Levine and L. Slade, "Water as a Plasticizer: physico-chemical aspects of low-moisture polymeric systems", in *Water Science Reviews*, vol. 3, F. Franks, Ed., Cambridge University Press, London, pp. 79-185, 1988.
U.S. Appl. No. 14/200,441, filed Mar. 7, 2014, Zasypkin, et al.
U.S. Appl. No. 14/218,400, filed Mar. 18, 2014, Zasypkin, et al.

* cited by examiner

*Primary Examiner* — Snighda Maewall
(74) *Attorney, Agent, or Firm* — Oblon, McClelland, Maier & Neustadt, L.L.P.

(57) ABSTRACT

Active encapsulation compositions which are stable in the glassy state at ambient temperatures are prepared by melt extrusion of a ternary carrier blend comprising of 1) a food polymer, 2) a spice or herb, and 3) a low molecular weight sugar or polyol. Such glassy matrices are useful for the encapsulation of encapsulates, in particular, flavors and medications.

34 Claims, 1 Drawing Sheet

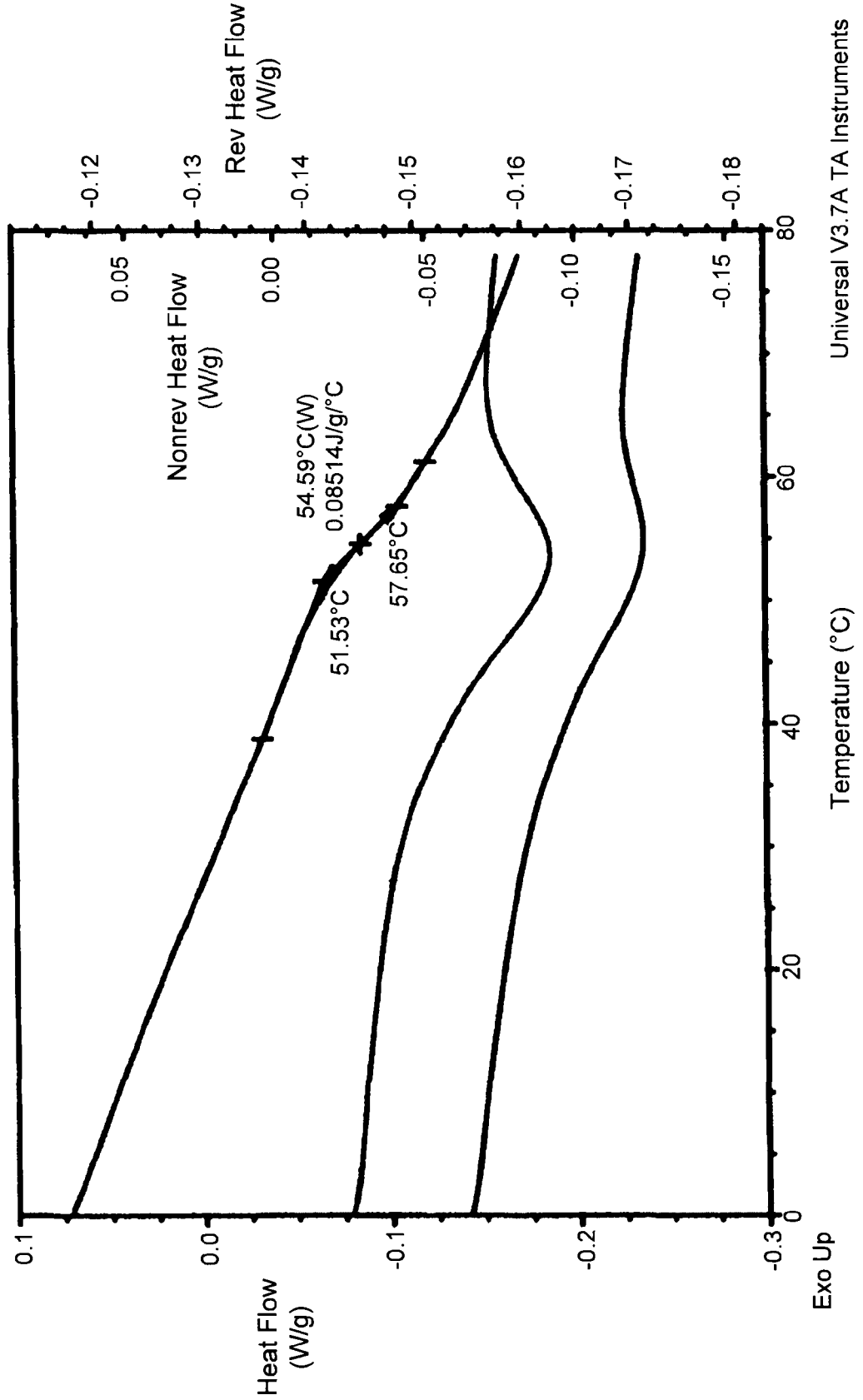

MELT EXTRUSION ENCAPSULATION OF FLAVORS AND OTHER ENCAPSULATES IN A CARRIER CONTAINING SPICES AND HERBS

CROSS REFERENCES TO RELATED APPLICATIONS

This application claims priority to U.S. Provisional Patent Application No. 61/325,099, filed on Apr. 16, 2010.

BACKGROUND OF THE INVENTION

1. Field of the Invention

The present invention relates to encapsulation compositions in which an encapsulate is encapsulated in a glassy matrix by a process known as melt extrusion. More particularly, the present invention relates to flavor encapsulation compositions in which a flavoring agent is encapsulated by melt extrusion in a glassy matrix containing spices and herbs as a part of the matrix. Incorporation of spices and herbs in the matrix creates an active carrier protecting and modulating the encapsulated flavoring agents. The present invention also relates to processes for preparing such compositions.

2. Discussion of the Background

The encapsulation of encapsulates is an area of active research. In particular, the encapsulation of encapsulates such as medications, pesticides (including insecticides, nematocides, herbicides, fungicides, microbiocides, etc.), preservatives, vitamins and flavoring agents is desired for a number of reasons. In the case of medications and pesticides, encapsulation may be desired to achieve controlled release of the medications or the pesticides. For vitamins, encapsulation may be carried out to protect the vitamins from air-oxidation and, thus, to extend shelf life of the vitamins. In the case of flavoring agents, the encapsulation may be carried out to place the flavorings in an easily metered form which will release the agent at a controllable event, such as the addition of water.

It is generally known to skilled practitioners in the field of flavor encapsulation that the current practical commercial processes leading to stable, dry flavors are limited in great part to spray drying and extrusion fixation. The former process requires emulsification or solubilization of the flavor in an aqueous carrier containing the encapsulation solids, followed by rapid drying in a high temperature, high velocity gas stream and collection as a low-density bulk solid.

While spray drying accounts for the majority of commercially encapsulated flavor materials, several limitations of the process are evident. Low molecular weight components of complex or natural flavor mixtures generally exhibit high vapor pressures and are usually lost or disproportionate during the process. The resultant flavor-carriers are porous and difficult to handle. In addition, deleterious chemical reactions such as oxidation can result on surfaces exposed during and after drying. The final product, a dry, free flowing fine powder will release the encapsulate rapidly upon hydration whether rapid release is desired or not. Incorporation of spices or herbs in a significant amount in the solubilized carrier is not practical for the reason of swelling of a spice or an herb powder in water, resulting in a high viscosity and clogging atomizing wheels or nozzles during spray drying.

Some other encapsulation processes may include freeze drying, drum drying and tray drying. These processes have marginal significance due to a high processing cost and relatively poor protection of encapsulates, compared to spray drying and extrusion. The processes of drying are slow in the case of freeze and tray drying resulting in a weak glassy character generated by slow drying rather than quick cooling. Volatile flavor losses are very significant. Drum drying could be a fast process; however, loss of volatile components is very significant on the contact with a high temperature surface. All the above processes require a milling step further weakening the flavor. Moreover, the preparation step involves making a slurry where spices and herbs will swell and form a viscous dispersion that is difficult to control and process.

U.S. Pat. No. 3,971,852 discloses the use of a modified starch, gums and other food polymers with low molecular weight polyhydroxy compounds and spray drying to yield a glassy matrix with encapsulated oil at a maximum of 70-80% by volume. The system forms a shell surrounding the oil flavoring but is limited to lipophilic flavoring agents.

U.S. Pat. No. 4,532,145 discloses a process for preparing compositions in which a volatile flavorant is fixed by spray drying from a carrier solution made up of 10-30% of a low molecular weight component such as a sugar or edible food acid with the balance of the solids being a maltodextrin carbohydrate in the amount of 70-90%.

U.S. Pat. No. 5,124,162 discloses a carrier mixture composed of mono- and disaccharides (22-45%), maltodextrins (25-50%), and a high molecular weight carbohydrate such as chemically modified starch or gum acacia (10-35%) to which volatile flavoring agents are added and the subsequent dispersion is spray dried to yield a free flowing powder with a bulk density of 0.50 g/cc.

A number of technical issues are unmet by these approaches. First, thermally sensitive flavors undergo undesirable reactions including oxidation, rearrangements, and hydrolysis. Secondly, volatile components are lost or disproportionate during atomization and evaporation in the dryer. Finally, spices and herbs are not included in the compositions.

A second process route, melt injection, has been utilized to advantage with lipid-based flavors. In this technology, a melt is prepared by boiling off sufficient water from a high solids carbohydrate syrup, adding flavoring oils with an emulsifier, agitating under pressure to emulsify the oil in the melt and injecting the mixture into a chilling, dehydrating solvent bath to obtain fine rod-like filaments. After solvent removal, the matrix is reduced in size and, in some cases, coated with an anti-caking agent before being packed. See, e.g., U.S. Pat. Nos. 2,809,895; 2,856,291; and 3,704,137. Subsequent improvements in the art are disclosed in U.S. Pat. No. 3,314,803 for the encapsulation of volatiles such as acetaldehyde, and in U.S. Pat. No. 4,707,367, which discloses encapsulation of up to 35% by weight of flavor oil in the glassy matrix.

U.S. Pat. No. 4,689,235 discloses the use of modified starch-maltodextrin carriers in the range of 5 parts modified starch/95 parts maltodextrin to 95 parts modified starch/5 parts maltodextrin. The carrier is dissolved to form a syrup, water is cooked off, flavor is added and emulsified, and the melt is injected into a solvent bath.

An alternative route to encapsulating flavors is disclosed in U.S. Pat. No. 4,230,687. In this approach, high molecular weight carriers such as proteins, starches and gums are plasticized by addition of significant amounts of water in the presence of the encapsulate and subjected to a high shear dispersing process. The rubbery or plastic matrix with encapsulate is then extruded, recovered and dried to yield a stable product.

Another alternative process, melt extrusion, can be utilized for flavor fixation and encapsulation. In this process, a melting system, i.e., an extruder is employed to form the carrier melt in a continuous process. The encapsulated flavor is either admixed or injected into the molten carbohydrate carrier.

U.S. Pat. No. 4,232,047 discloses the use of a matrix comprising a fused encapsulating material selected from the group consisting of starches, cereal flour, modified starches, gums, proteins, and mixtures thereof to encapsulate essential oils, oleoresins, and mixtures. The composition is melted in the presence of 10% to 40% by weight of water and extruded under non-puffing conditions. The flavor agent forms a micro dispersion in the glasseous melt.

U.S. Pat. No. 5,972,395 discloses the use of a matrix composed of 15 to 40% of a high molecular weight carrier, preferably a maltodextrin and at least 40% of a low molecular weight carbohydrate, sugar polyol, or adipic acid. The matrix is extruded to yield a solid matrix characterized as a glass.

U.S. Pat. Nos. 5,087,461 and 5,009,900 disclose utilizing a composition consisting of a modified food starch, maltodextrin, polyol, and mono- and disaccharide components. The starch is a chemically-modified water-soluble starch and is used in the amount of 40 to 80% of the total mixture. The balance of the composition is comprised of 10 to 40% maltodextrin, 5 to 20% corn syrup solids or polydextrose, and 5 to 20% mono- or disaccharide. This matrix is said to balance processing response with glass matrix character.

U.S. Pat. No. 5,756,136 discloses the encapsulation of cinnamic aldehyde in a matrix containing at least 25% of a whey protein isolate. The resulting encapsulate exhibits a control release functionality and protection for yeast-leavened dough.

U.S. Pat. Nos. 6,652,895; 6,416,799; 6,187,351; 5,603,971; and 5,897,897 disclose the use of a series of extrusion matrix compositions. The use of water to plasticize the matrix in the extrusion process yields an encapsulated flavor matrix characterized by glass transition temperatures greater than 40° C. In U.S. Pat. No. 6,652,895, a composition containing a carboxylate or sulfate containing food polymer and the presence of calcium ions in the melt is disclosed. In U.S. Pat. No. 6,416,799, a composition containing a maltodextrin with buffering organic acid-acid salts is disclosed. In U.S. Pat. No. 6,187,351, a composition containing 2 to 45% of a food polymer, 25 to 80% of a maltodextrin, and 10 to 30% of a mono- or disaccharide or 24 D.E. to 42 D.E. corn syrup solids is disclosed. The matrix is dry blended, fed into the extruder with the required water plasticizer and flavor, and the resulting encapsulate is obtained as a glassy solid exhibiting a glass transition temperature greater than 40° C. The disclosed polymers include modified celluloses, high methoxy pectin, gum arabic (*acacia*), locust bean gum, guar gum, and lesser gums such as gum ghatti, gum tragacanth and gum karaya. Also disclosed are proteins such as gelatin and casein, microbial gums such as xanthan and gellan, pregelatinized starches in addition to other carbohydrate polymers such as inulins, beta-glucans and konjac flour.

U.S. Patent Application 2002/0189493 discloses the use of majority, single polymer component compositions with melt extrusion encapsulation. In one case, a matrix composed of a binary polymer composition selected from the group of gelatin, hydrolyzed gelatin, larch gum and gum arabic at 0 to 50% of the individual polymers is disclosed.

U.S. Patent Application 2002/0187223 teaches the use of prehydrated agar agar (at 1-7% levels) with other carriers which are mixed with a flavor, extruded and dried to form a glassy matrix encapsulating media.

U.S. Pat. No. 4,816,298 discloses the preparation of a cold-water dispersible granular composition comprising a plasticizer and thermally moldable polymers. The polymers are selected from the group of methyl cellulose, hydroxypropyl methylcellulose, carboxymethyl cellulose, and hydroxypropyl cellulose and are extruded at an elevated temperature with plasticizer to yield a cold-water dispersible matrix.

In a number of the cited patents which disclose melt extrusion, the matrix compositions were carefully defined to accommodate processing limitations of the extruder, as well as to generate a stable matrix in the glassy state characterized by a glass transition temperature of greater than 40° C. The cited patents describe liquid flavor, essential oils, oleoresins, processed flavors, medications, pesticides, and vitamins as encapsulates.

Formation of a matrix in the glassy state is of particular value for encapsulation of water-soluble flavorings and extracts. The role of water as a plasticizing agent conflicts with the desired results, because water has the effect of lowering the glass transition temperature (Tg) of the glassy matrix. In model studies of a number of food carbohydrate systems, the upper limit of water content is approximately 7 to 10 wt. % for lower molecular weight components such as mono- and disaccharides, maltodextrins, food polymers and combinations of these agents. At higher water contents, the Tg is lowered to the extent that the matrix is in the undesirable rubbery, plastic or fluid state at room temperatures.

In order to insure a higher Tg, several options are available. By limiting the class of encapsulate materials to lipophilic materials such as citrus oils, plasticizing moisture can be removed by a boil off process as described in U.S. Pat. Nos. 2,856,291; 2,809,895; 3,314,803; 3,704,137; and 4,707,367. Alternatively, the use of melt injection limits the flavoring agents to materials with lower vapor pressure which can be admixed to the composition before melting. Flavorings which are in the form of aqueous extracts, water, or alcohol-water solutions will result in a product with a Tg much below 25° C. leading to plastic flow and loss of volatiles upon storage.

Similarly, in U.S. Pat. Nos. 5,009,900 and 5,972,395, the flavorings are limited to those with limited volatility, and total moisture level in the product is less than 11% by weight. Many of the key top notes and unique flavor components of complex flavors have high vapor pressures at room temperature and are not easily encapsulated by such a process.

Matrix improvements for the continuous melt extrusion process are described in U.S. Pat. Nos. 6,652,895; 6,416,799; 6,187,351; 5,603,971; and 5,897,897. The use of modified starch and food polymers with low molecular weight carbohydrate plasticizers is detailed to yield encapsulates in a glassy matrix with a Tg greater than 40° C. However, with these matrices, the flavor loads are generally limited to 10 wt. % or less. Encapsulates described were medications, pesticides, vitamins, preservatives, and flavoring agents, wherein the flavoring agent is selected from the group consisting of natural extracts, oleoresins, essential oils, protein hydrolyzates, aqueous reaction flavors, compounded natural flavors, and artificial flavors.

Preparation of a solid in the glassy state is dependent upon both matrix composition and the process used to generate the encapsulating material. The advantages of retaining the glass form of the matrix include increased physical stability of the solid, reduced loss of incorporated volatiles, and reduction of deleterious intermolecular reactions and oxidation. A detailed discussion of the physical chemistry of water-food polymer interactions relating to the glassy state can be found in H. Levine and L. Slade, "Glass Transitions in Foods," in *Physical Chemistry of Foods*, H. Schwartzberg and R. Hartel, Eds., Marciel Dekker, New York, pp. 83-205, 1992; and in H. Levine and L. Slade, "Water as a Plasticizer: physico-chemical aspects of low-moisture polymeric systems," in *Water Science Reviews*, vol. 3, F. Franks, Ed. Cambridge University Press, London, pp. 79-185, 1988, which are incorporated herein by reference. The role of water as a plasticizer with food polymers, as well as the relationships between molecular compositions and dynamics of interactions between various components, are discussed in these references.

It is important to mention that melt extrusion is not a drying process. It generates glassy compositions by melting matrix components, followed by a quick cooling of the melt. Optionally, in-process or post-processing drying could be applied to further control moisture and other properties of the compositions. However, drying is not essential for the formation of glassy encapsulation compositions. Water or aqueous solutions used as a plasticizer are added in the amounts not preventing formation of a glassy matrix with the glass transition temperature above ambient temperature. In other words, quick cooling of the matrix makes it glassy without significant water evaporation. This distinguishes the melt extrusion process from spray-, drum-, or tray drying where a glassy matrix may be obtained mainly though evaporation of water from a slurry.

Spices and herbs in their original and ground powdered form possess unique flavor properties. More recently it has been recognized that spices and herbs contain potent antioxidants that may have protective properties for oils and flavors. The same antioxidants may be health beneficial. Thus, there remains a need for encapsulation compositions in which an encapsulate is encapsulated in an active carrier which is stable in the glassy state at ambient or slightly elevated temperatures and contains a significant amount of spices and herbs in addition to liquid or solid encapsulates. These active carriers can exhibit unique flavor interactions with encapsulates and modulate a flavor imparted by encapsulates. In turn, flavors may modulate flavor characteristics imparted by the active carrier and have an effect on bioavailability or other antioxidant or protective functions of spices and herbs. There is also a need to mask, modify or mitigate some of the intense background notes introduced by either spices, herbs or encapsulates. The glassy carriers can preserve, modulate and control release of encapsulates. There is also a need to preserve labile and sensitive flavors with natural antioxidants introduced by spices and herbs constituting a significant part of the active carrier.

SUMMARY OF THE INVENTION

Accordingly, it is one object of the present invention to provide novel encapsulation compositions.

It is another object of the present invention to provide novel encapsulation compositions in which an encapsulate is encapsulated in a carrier which is stable in the glassy state at ambient temperatures.

It is another object of the present invention to provide novel encapsulation compositions in which an encapsulate is encapsulated in a carrier which is stable in the glassy state at ambient temperatures and contains spices and herbs as a part of the carrier composition.

It is another object of the present invention to provide novel flavor encapsulation compositions in which a flavoring agent is encapsulated in a carrier which is stable in the glassy state at ambient temperatures and contains spices and herbs as a part of the carrier composition.

It is another object of the present invention to provide novel flavor encapsulation compositions which are amenable to the encapsulation of volatile or sensitive flavor components and containing spices and herbs as a part of the carrier composition.

It is another object of the present invention to provide novel flavor encapsulation compositions which exhibit selected controlled release functionality in product applications.

It is another object of the present invention to provide novel flavor encapsulation compositions which exhibit unique flavor delivery, antioxidant functionality and health benefits in product applications.

It is another object of the present invention to provide novel processes for preparing such encapsulation compositions.

These and other objects, which will become apparent during the following detailed description, have been achieved by the inventor's discovery that it is possible to prepare food polymer-based glassy carriers, which contain up to 40% spices and herbs and have sufficiently high Tg to prevent plastic flow and caking at ambient temperatures, by blending spices, herbs, and one or more food polymers with an aqueous plasticizer in the melting zone of an extruder, adding the encapsulate to the molten matrix, and extruding the resulting mixture. The aqueous plasticizer may be used in an amount below 10% by weight of the total composition in order to prevent swelling of spices and herbs and to keep a low viscosity of the melt.

Thus, the present invention provides (1) An extrusion encapsulation composition, comprising:
(A) an encapsulate, encapsulated in:
(B) a glassy matrix,
wherein:
said glassy matrix is a composition, comprising: 5 to 40% by weight, based on the total weight of said matrix (B), of a spice or a herb; 5 to 40% by weight, based on the total weight of said matrix (B), of a component selected from the group consisting of a low molecular weight sugar, a low molecular weight polyol, a corn syrup solid, and mixtures thereof; and 40 to 90% by weight, based on the total weight of said matrix (B), of at least one component selected from the group consisting of an n-octenylsuccinic acid anhydride-modified starch, maltodextrin, larch gum, gum Arabic, inulin, cyclodextrin, polydextrose, and hydrolyzed gelatin, said extrusion encapsulation composition is prepared by a process comprising:
(i) blending the components of a matrix composition (B) as a dry powder;
(ii) mixing the dry blend of a matrix composition (B) with water as a plasticizer and an encapsulate (A) in an extruder, to obtain a melted mixture comprising encapsulate (A) and matrix (B); and
(iii) extruding said melted mixture, to obtain said composition, wherein said encapsulate (A) is encapsulated in a glassy matrix of said matrix composition (B),
said glassy extrusion encapsulation composition contains less than 10% water and an encapsulate (A) in the range from 0.1% to 20% by weight, based on the total weight of the glassy extrusion encapsulation composition.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 is an example of a Modulated Differential Scanning calorimetry (MDSC) graph of a flavor encapsulated by melt extrusion. The extrudate matrix (carrier) is the composition of Example 2. Sunflower oil used as an oil soluble flavor was encapsulated at 6% load. The glass transition temperature was calculated from the reversing component of the heat flow (top curve). The non-reversing component of the heat flow is shown in the middle. The total heat flow curve is shown at the bottom.

DETAILED DESCRIPTION OF THE PREFERRED EMBODIMENTS

As noted above, the present invention has been made possible in part, by the inventor's discovery that it is possible to prepare, by extrusion, matrices which contain 5% to 40% spices and herbs in combination with 40% to 90% of selected food polymers and 5% to 40% low molecular weight sugars and polyols, based on the weight of the matrix ingredients, which have a glass transition (Tg) sufficiently high such that the glassy matrix is stable at ambient temperatures, with the use of aqueous plasticizer at the levels below 10% of the weight of the matrix components. This discovery is a surprising result considering the well-known large glass-transition-lowering effect of water in carbohydrate and protein based systems. In addition, it was surprisingly found by the inventor that the selected food polymers which normally exhibit extremely large viscosities in the hydrated state can be melted and exhibit plastic flow compatible with the extrusion process to yield a matrix which rapidly solidifies and sets into the desirable glassy state. The choice and function of the food polymers must be carefully balanced in terms of composition, type and use levels. The adjustment of desirable plastic flow properties can be managed in part by the use of additional plasticizers such as glycerine, propylene glycol in addition to primary plasticizer: water. Finally, the most surprising discovery is that 5% to 40% of spices or herbs can be incorporated into the matrix without imparting too high viscosity to the polymer melt as long as the total level of plasticizers is below 10%, based on the total weight of the matrix components. Such a low level of the plasticizers prevents hydration and swelling of water insoluble spices and herbs in the melt, thus preventing development of high viscosity of the melt and resulting in a glass transition temperature (Tg) sufficiently high such that the glassy matrix is stable at ambient temperatures.

Thus, in a first embodiment, the present invention provides encapsulation compositions in which (A) an encapsulate is encapsulated in (B) a glassy matrix which is a composition, comprising: 5 to 40% by weight, based on the total weight of said matrix (B), of a spice or an herb; 5 to 40% by weight, based on the total weight of said matrix (B), of a component selected from the group consisting of a low molecular weight sugar, a low molecular weight polyol, a corn syrup solid, and mixtures thereof; and 40-90% by weight, based on the total weight of said matrix (B), of at least one component selected from the group consisting of an n-octenylsuccinic acid anhydride-modified starch, maltodextrin, larch gum, gum Arabic, inulin, cyclodextrin, polydextrose, and hydrolyzed gelatin.

The extrusion encapsulation composition is prepared by a process comprising: (i) blending the components of a matrix composition (B) as a dry powder, (ii) mixing the dry blend of a matrix composition (B) with water as a plasticizer and an encapsulate (A) in an extruder, to obtain a melted mixture comprising encapsulate (A) and matrix (B); and (iii) extruding said melted mixture, to obtain said composition, wherein said encapsulate (A) is encapsulated in a glassy matrix of said matrix composition (B).

The glassy extrusion encapsulation composition contains less than 10% water and an encapsulate (A) in the range from 0.1% to 20% by weight, based on the total weight of the glassy extrusion encapsulation composition. Preferably, the composition contains less than 9% by weight water, even more preferably, less than 8% by weight water. A preferred lower limit for the amount of water is 2% by weight, more preferably 3% by weight.

In a preferred embodiment, matrix composition (a) comprises 10 to 30% by weight, more preferably 15 to 25% by weight, based on the total weight of said matrix (B), of a spice, an herb, or a blend thereof; 10 to 30% by weight, based on the total weight of said matrix (B), of a component selected from the group consisting of a low molecular weight sugar, a low molecular weight polyol, a corn syrup solid, and mixtures thereof; 60 to 80% by weight, more preferably 60 to 70% by weight, based on the total weight of said matrix (B), of at least one component selected from the group consisting of an n-octenylsuccinic acid anhydride-modified starch, maltodextrin, larch gum, gum Arabic, inulin, cyclodextrin, polydextrose, and hydrolyzed gelatin.

Suitable n-octenylsuccinic acid anhydride-modified starches (OSAN-modified starches) and other food polymers are described in more detail immediately below.

The modified starches consist of a group of n-octenylsuccinic anhydride modified starches (OSAN-starch). The starches may be concomitantly modified by dextrinization and chemically derivatized with n-octenylsuccinic acid anhydride. Alternatively, the starch may undergo initial chemical or enzymatic hydrolysis followed by derivatization with n-octenylsuccinic acid anhydride. Examples of such modified OSAN-starches are sold under the trade names: Capsul, Amiogum, Hi-Cap 100, Emcap 12634, Emcap 12639, Miracap, and National 780487 among others.

Maltodextrins are also suitable carbohydrate food polymers. These polymers are derived from the partial hydrolyzed forms of corn, rice, wheat, or potato starches utilizing suitable acid or enzymatic catalysis. The maltodextrins are defined as having a Dextrose Equivalent (DE) of less or equal 20. The most suitable maltodextrins are the 5 DE, 10 DE, 15 DE and 18 DE maltodextrins.

Hydrogenated starch hydrolyzates (HSH) are the products obtained from the hydrolysis of a starch to generate maltodextrin oligomers. These oligomers are then hydrogenated to convert the terminal reducing sugar moiety to an oligomer with a non-reducing terminal polyol. For the purpose of this invention HSH are included in the group of low molecular weight polyols.

Polydextrose is the glucosyl homopolymer resulting from the condensation of glucose in the presence of an acidic catalyst.

Inulin is a naturally occurring polysaccharide produced by many types of plants. It belongs to a class of fibers known as fructans. Its flavor ranges from bland to subtly sweet (approx. 10% sweetness of sugar/sucrose). Inulin is composed mainly of fructose units, and typically has a terminal glucose. The fructose units in inulin are joined by a $\beta(2\rightarrow1)$ glycosidic bond. In general, plant inulin contain between 20 and several thousand fructose units. Smaller compounds are called fructooligosaccharides, the simplest being 1-ketose, which has 2 fructose units and 1 glucose unit. Depending on the source of inulin it could also be labeled as chicory root fiber, chicory root extract, artichoke extract or an extract from another plant or a plant part.

Cyclodextrins are a family of compounds made up of α-D-glucose units. The glucose unites are linked by α-1-4 bonds to form a cyclical structure with a hydrophilic exterior and a hydrophobic cavity. Cyclodextrins are produced from starch by means of enzymatic conversion. Typical cyclodextrins contain a number of glucose monomers ranging from six to eight units in a ring. They are denoted as following: α-cyclodextrin contains six, β-cyclodextrin seven, and γ-cyclodextrin eight glucose units.

Hydrolyzed gelatin is produced by hydrolysis of a gelatin. Gelatin, the soluble protein extract from collagen, comes from various animal sources and in different forms. There are acid-extracted and base-extracted forms of gelatin. The key difference of the two forms being in the isoelectric point of the resultant, soluble polymer. Sources of the collagen used for extraction to generate the gelatin include cattle hides and pork skins. The type and degree of extraction lead to various grades of gelatin. Acid hydrolysis of the collagen leads to Type A acid gelatin. Similarly base hydrolysis and extraction leads to a Type B gelatin. The isoelectric points are generally in the pH range of 7 to 9 for Type A; and 4.7 to 5.1, for Type B. Gelatins are generally characterized by their gelling strength in terms of Bloom using a standardized procedure and a Bloom gelometer. Commercial gelatins vary from 50 to 300 Bloom with the high values indicating stronger gels (see M. Glicksman, *Gum Technology in the Food Industry*, Academic Press, pp. 359-397, 1969, which is incorporated herein by reference). The particular gelatins which are most compatible with the extrusion encapsulation process of the present invention are the 50 to 75 Bloom gelatins of both type A and B.

Hydrolyzed gelatins are preferred in this invention. They are derived from the standard gelatins by an additional hydrolysis step. The result is a hydrolyzed, water soluble, non-gelling form of the food protein. Generally, molecular weights of the hydrolyzed gelatins are in the range from 10,000 to 100,000. Amidated gelatins may also be used.

Gum arabic is an exudate gum obtained from *Acacia* trees. The main species are *Acacia senegal* and *Acacia seyal*. Gum arabic is a branched molecule with a main chain of (1→3)-linked-β-D-galactopyranosyl units having side chains, consisting of (1→3)-linked β-D-galactopyranosyl units, joined to it by (1→6)-linkages. The resulting side chains consist of various acidic sugars (see *Industrial Gums*, R. Whistler and J. BeMiller, Eds., 3rd Edition, Academic Press, pp. 311-318, 1993, which is incorporated herein by reference). The hydrocolloid shows enhanced solubility and relatively low viscosities in solutions of 30 to 40 wt. % solids. Generally, the *A. senegal* gum is used to make beverage emulsions, while the *A. seyal* gum is used for spray drying applications. In spray drying, the key functional characteristics of the polymer are its emulsifying capacity, good film-forming properties upon drying and reasonably low aqueous viscosity. One key commercial specification for the *A. seyal* product is the degree of color contributed by the gum. With some darker lots of the gum, a bleaching step is sometimes added to lighten the product color by oxidation. Unexpectedly it was discovered by the present inventors that unbleached *A. seyal* or *A. senegal* can be extruded in a manner which protects the freshly extruded molten extrudate from flashing off flavor volatiles coming from a flavor or spices and herbs in the active carrier.

Larch gum or arabinogalactan is the hydrocolloid extracted from the Larch tree. The arabinogalactan is composed of galactose and arabinose units in a 6:1 ratio, with a trace of uronic acid. The molecular weights of the major fractions of arabinogalactan in larch gum are 16,000 and 100,000. Glycosyl linkage analysis of arabinogalactan is consistent with a highly branched structure comprising a backbone of 1,3-linked galactopyranose connected by 1,3-glycosidic linkages.

In the use of mixed polymers such as an OSAN-modified starch with a gum, hydrolyzed gelatin or mixed polymer formulations, the response of the mixed polymer melt within the extruder must be empirically determined. In some cases the presence of two glass transitions in the resultant glassy solid could be observed. The explanation for the presence of two glass transitions can be developed by one of two possible considerations. In the first case the selected extruded polymers are immiscible in the molten state forming the equivalent of a polymer-in-polymer "emulsion." Alternatively, the two polymers may be miscible but are incompletely mixed during melting and mixing in the short residence time occurring during the melt extrusion process. There is extremely limited knowledge of this phenomenon in the food literature. The interactions of a large number of binary polymer systems in the aqueous-carbohydrate plasticizing environment of the melt extrusion process can only be determined experimentally.

The present composition contains as a powder 5% to 40%, preferably 10% to 30%, based on the total weight of the matrix composition, of spices and herbs including those disclosed in: *Herbs, Spices and Flavorings*, 1982, Tom Stobart, The Overlook Press, Woodstock, N.Y., Wiley, New York, 320 p.; *The Encyclopedia of Herbs, Spices, and Flavorings*, 1992, Contr. Ed. E. L. Ortiz, Dorling Kindersley, Inc., New York, 288 p., both of which are incorporated herein by reference. Suitable spices and herbs include ajowan, alexanders, allspice, almond, aloe, angelica, anise, anise-pepper, annatto, areca nut, asafoetida, avens, balm, sweet basil, bay, bergamot, borage, calamint, chamomile, candlenut, caper, caraway, cardamom, catmint, celery, garden chervil, chicory, chive, cinnamon, cassia, citron, clary, clove, coconut, coffee, cola, coriander, costmary, cress, cumin, curry leaf, dill, fennel, fenugreek, galangal, garlic, garlic mustard, ginger, grains of paradise, hop, hyssop, juniper, leek, lemon grass, liquorice, lovage, mace, malt, marjoram, mint, dried edible mushrooms, mustard, nutmeg, onion, oregano, parsley, pepper, poppy, rosemary, saffron, sage, samphire, sesame, star anise, tarragon, thyme, turmeric, vanilla.

Spices and herbs are preferably added to the composition in a dry form: as a dry powder. Spices and herbs are typically sterilized then dried to a moisture content in the range from 1% to about 10% by weight. The most preferred moisture of spices and herbs for the process of this invention is in the range from 2% to 7% by weight. Usually, dried spices and herbs are reduced in size by milling and/or sieving to sizes most suitable for applications. For the process of this invention the preferred size of the dry particles of milled spices and herbs is in the range from 20 microns to about 2 millimeters, even more preferred range is from 50 um to 1 mm, the most preferred range is from 70 um to 500 um.

It is also within the scope of the present invention that spices and herbs are additionally processed before melt extrusion. Besides the above-mentioned sterilization, drying, milling, and sieving, spices and herbs could be heated, roasted, blended, or treated with a solvent which is subsequently removed. Some actives or extractives could be removed from spices and herbs by a solvent extraction. Some specific parts of spices and herbs could be used instead of whole spices and herbs in their original or a processed form. These parts could be additionally processed as described above.

The present composition also contains 5 to 40% by weight, preferably 10 to 35% by weight, based on the total weight of the matrix composition, of a component selected from the group consisting of a low molecular weight sugar, a low molecular weight polyol, a corn syrup solid, and mixtures thereof. Examples of suitable sugars include mono- and disaccharides (including glucose, sucrose, maltose, fructose, galactose, ribose, xylose, lactose, cellobiose, trehalose), invert syrups, molasses, and corn syrups. The preferred sugars are glucose and maltose.

Polyols are a group of lower molecular weight ingredients known as polyhydric agents. Simpler polyols include glycerine, and propylene glycol. Examples of other polyols include erythritol, lactitol, mannitol, sorbitol, maltitol, isomalt, dulcitol, xylitol, hydrogenated corn syrups, hydrogenated glucose syrups, hydrogenated maltose syrups, and hydrogenated lactose syrups. The preferred polyols are mannitol, sorbitol, and isomalt. Suitable corn syrup solids are the 36 to 42 D.E. corn syrup solids. Hydrogenated starch hydrolyzates (HSH) are the products obtained from the hydrolysis of a starch to generate maltodextrin oligomers. These oligomers are then hydrogenated to convert the terminal reducing sugar moiety to an oligomer with a non-reducing terminal polyol. HSH are included in the groups of low molecular weight polyols.

The term encapsulate as used in the present invention, includes agents such as medications, pesticides, preservatives, vitamins, food acids, salts, flavoring agents, perfumery chemicals and fragrances, and food colorants both synthetic and natural. Suitable medications include antacids, anti-inflammatory substances, coronary vasodilators, cerebral vasodilators, peripheral vasodilators, anti-infectives, psychotropics, anti-manics, stimulants, antihistamines, laxatives, decongestants, vitamins, gastrointestinal sedatives, antidiarrheal preparations, antianginal drugs, antiarrhythmics, antihypertensive drugs, vasoconstrictors, migraine treatments, anticoagulants, antithrombotic drugs, analgesics, antipyretics, hypnotics, sedatives, antiemetics, antinauseants, anticonvulsants, thyroid and antithyroid preparations, diuretics, antispasmodics, uterine relaxants, mineral and nutritional additives, antiobesity drugs, anabolic drugs, erythropoietic drugs, antiasthmatics, expectorants, cough suppressants, mucolytics, antiuricemic drugs, and other drug substances such as topical analgesics, local anesthetics and the like.

Suitable pesticides include insecticides, nematocides, fungicides, herbicides, and microbicides. Insecticides, which may be encapsulated in the present compositions include those disclosed in Kirk-Othmer, *Encyclopedia of Chemical Technology,* 4th Ed., vol. 14, Wiley, New York, pp. 524-602, 1995, and 3rd Ed., vol. 13, pp. 313-485, 1981, both of which are incorporated herein by reference. Suitable nematocides include, e.g., methyl N'N'-dimethyl-N-[(methylcarbamox) oxy]-1-thiooxamimidate (oxamyl) and those disclosed in Kirk-Othmer, *Encyclopedia of Chemical Technology,* 4th Ed., vol. 24, Wiley, New York, pp. 830-831, 1997, and 3rd Ed., vol. 18, pp. 305-308, 1982, both of which are incorporated herein by reference. Suitable fungicides include those disclosed in Kirk-Othmer, *Encyclopedia of Chemical Technology,* 4th Ed., vol. 12, Wiley, New York, pp. 204-227, 1994, and 3rd Ed., vol. 11, pp. 490-498, 1980, both of which are incorporated herein by reference. Suitable herbicides include those disclosed in Kirk-Othmer, *Encyclopedia of Chemical Technology,* 4th Ed., vol. 13, Wiley, New York, pp. 73-136, 1995, and 3rd Ed., vol. 12, pp. 297-351, 1980, both of which are incorporated herein by reference. Suitable antibiotics and antimicrobials include those disclosed in Kirk-Othmer, *Encyclopedia of Chemical Technology,* 4th Ed., vol. 2, Wiley, New York, pp. 854-1018, 1992, and vol. 3, pp. 1-346, 1992, both of which are incorporated herein by reference. Suitable vitamins include those disclosed in Kirk-Othmer, *Encyclopedia of Chemical Technology,* 4th Ed., vol. 25, Wiley, New York, pp. 1-17, 1998, and 3rd Ed., vol. 24, pp. 1-277, 1984, both of which are incorporated herein by reference. Suitable food additives, in addition to flavoring agents, include those disclosed in Kirk-Othmer, *Encyclopedia of Chemical Technology,* 4th Ed., vol. 11, Wiley, New York, pp. 805-833, 1994, and 3rd Ed., vol. 11, pp. 146-163, 1980, both of which are incorporated herein by reference.

The term flavoring agent includes spice oleoresins and oils derived from allspice, basil, capsicum, cinnamon, cloves, cumin, dill, garlic, marjoram, nutmeg, paprika, black pepper, rosemary and turmeric; essential oils: anise oil, caraway oil, clove oil, eucalyptus oil, fennel oil, garlic oil, ginger oil, peppermint oil, onion oil, pepper oil, rosemary oil, and spearmint oil; citrus oils such as orange oil, lemon oil, bitter orange oil and tangerine oil; alliaceous flavors: garlic, leek, chive, and onion; botanical extracts: arnica flower extract, chamomile flower extract, hops extract, and marigold extract; botanical flavor extracts: blackberry, chicory root, cocoa, coffee, kola, licorice root, rose hips, sarsaparilla root, sassafras bark, tamarind and vanilla extracts; protein hydrolysates: hydrolyzed vegetable protein (HVPs), meat protein hydrolysates, milk protein hydrolysates; and compounded flavors both natural and artificial including those disclosed in S. Heath, *Source Book of Flavors,* Avi Publishing Co. Westport, Conn., pp. 149-277, 1981, which is incorporated herein by reference. Representative flavor compounds are for example: benzaldehyde, diacetyl(2,2-butanedione), vanillin, ethyl vanillin and citral (3,7-dimethyl-2,6-octadienal). The flavoring agent may be in the form of oil, aqueous solution, non-aqueous solution or an emulsion. Flavor essences, i.e., the water-soluble fraction derived from fruit or citrus can be utilized although at lower levels than the ingredients referenced above. As will be described more fully below, the present invention is particularly advantageous when the flavoring agent is itself a combination of volatile compounds with varying vapor pressures at ambient conditions.

Although the exact amount of encapsulate encapsulated in the matrix will depend, in part, upon the precise nature of the matrix, and the anticipated end use of final composition, the encapsulation compositions of the present invention will typically comprise 4 to 18% by weight, based on the total weight of the composition, of encapsulate. Preferably, the present encapsulation composition will comprise 6 to 10% by weight, based on the total weight of the composition, of encapsulate. The preferred encapsulate is a flavoring agent.

When the encapsulate is a lipophilic flavor, the encapsulate is dispersed in the glassy matrix of the final product usually with the aid of an emulsifier added to the lipophilic phase or in the matrix mixture. Emulsifiers such as distilled monoglycerides, ethoxylated monoglycerides, lactylated monoglycerides, acetylated monoglycerides, diacetyl tartaric acid esters of monoglycerides (D.A.T.E.M.'s), propylene glycol monoesters, sorbitan monostearate, sorbitan tristearate, polyglycerol esters, polyoxyethylene sorbitan monoester and triesters, sucrose esters, sodium stearoyl lactylate (S.S.L.), lecithin, hydroxylated lecithin, oleyl lactylic acid, lactylated esters of monoglycerides, lactylated fatty acid esters of glycerol and propylene glycol, and lactylated esters of propylene glycol monoglycerides, and the sodium and potassium salts of fatty acids can be employed singly or in combination. The emulsifier(s) is used at the level of 0.1 to 10% of the selected flavor. Preferred emulsifiers are the sorbitan polyoxyethylene monoesters.

In addition to the foregoing encapsulates, various optional ingredients such as conventionally used in the art, may be included in the compositions of the present invention. For example, colorings, sweeteners, food acids, salts, fragrances, diluents, flavor maskers, flavor enhancers, fillers, preservatives, antioxidants, stabilizers, lubricants, and the like may be employed herein if desired.

The present encapsulation compositions are prepared by melt extrusion at the moisture of the melt and the product below 10%, more preferably between 4% and 8% by weight of the total composition. The compositions could not be prepared by spray drying for the reason of swelling of spices and herbs in the presence of water above 10% by weight. Spray drying involves preparation of an aqueous dispersion or slurry, preferably, at total solids content above 30% for most efficient drying. This requirement can be met only with a few food polymers or low molecular weight components. Swollen particles of powdered spices and herbs will increase the viscosity and make the process impractical. For the same reason, extrusion of spices and herbs in the presence of 10% or higher moisture in the melt will make it impossible to form a glassy extrudate without additional drying. The present inventor has discovered that it is possible to prepare a glassy stable extruded composition at the moisture of the melt and the final product below 10%, preferably, between 4 and 8% by weight of the total composition. The glass transition temperature of the composition is above room temperature and preferably in the range between 35 and 55° C.

The present invention provides a process for preparing the present encapsulation composition, which comprises:

(i) mixing a matrix composition (B) with a liquid plasticizer and an encapsulate (A) in an extruder, to obtain a melted mixture comprising encapsulate (A) and matrix composition (B); and (ii) extruding said melted mixture.

In the present process, the liquid plasticizer may be any which is suitable for facilitating the formation of the melt in the extruder while at the same time affording a product which exists in the glassy state, rather than the plastic or rubbery state at room temperature. Suitable plasticizers include water; glycerol; propylene glycol; aqueous solutions of glycerol, propylene glycol, monosaccharides, and disaccharides; and invert and high fructose corn syrups. When the encapsulate is a flavor and the final product is intended to be used as a food additive, the plasticizer should be a food grade solvent. In one preferred embodiment, the present composition is prepared by utilizing water as the liquid plasticizer.

The plasticizer is added in an amount which results in the formation of a melt in the extruder, while at the same time affording a product which exists in the glassy state at room temperature. Thus, the amount of the plasticizer added may be selected to afford a product which has a Tg of at least 30° C., preferably at least 35° C., more preferably at least 40° C.

Suitable carbohydrates which are utilized as the non-polymeric component in the formulas and which function in a concomitant fashion as a plasticizer include mono- and disaccharides, trehalose, invert syrups, molasses, corn syrups, and 36 to 42 D.E. corn syrup solids. Suitable polyols are erythritol, sorbitol, mannitol, lactitol, maltitol, isomalt, dulcitol, xylitol, hydrogenated corn syrups, hydrogenated glucose syrups, hydrogenated maltose syrups, and hydrogenated lactose syrups. The preferred carbohydrates are glucose and maltose, and the preferred polyols are mannitol, sorbitol, and isomalt.

The matrix (B), along with the plasticizer forms a melt in the extruder. Although the mixing action of the extruder will supply heat to the matrix/plasticizer mixture, it will typically be necessary to supply additional heat to ensure formation of the melt. The encapsulate (A) is continuously added in a liquid phase to the feeding zone of the extruder by injection and mixed with the melted matrix/plasticizer mixture before exiting the extruder. In some embodiments, it may be preferred to add a non-aqueous, liquid plasticizer to the encapsulate phase.

In certain embodiments, a surface-active agent, i.e., an emulsifier can be added to the dry blend, or preferably added to the liquid flavor mix which is ultimately injected into the melting zone of the extruder. These emulsifiers can be from the class of distilled monoglycerides, mono- and diglyceride blends, propyleneglycol monoglycerides, lecithin, modified lecithins, acetylated monoglycerides, lactylated monoglycerides, lactylated fatty acid esters of glycerol and propylene glycol, and lactylated propyleneglycol monoglycerides, sorbitan esters, sorbitan-polyoxyethylene [20] monoglycerides, polyglycerol esters, DATEM's (diacetyltartarate esters of monoglycerides), succinylated esters of monoglycerides and polyoxyethylenepropylene copolymers, ethylene oxide-propylene oxide copolymers (Pluronics) and mixtures thereof. The most preferred surfactants are the sorbitan-polyoxyethylene [20] monoglycerides.

Preferred flavorants may be compounded flavors, essential oils, citrus oils, fruit extracts and essences, oleoresins and other forms. In some cases, the flavors can be diluted in a series of flavor solvents. These include fractionated coconut oils (medium chain triglycerides), propyleneglycol, glycerol, triacetin (glycerol triacetate) among others.

In a preferred embodiment, a twin screw extruder is used.

When the encapsulation composition exits the extruder, it may be cooled in ambient temperature air, or in chilled or sub-ambient temperature air, or by passing through a liquid bath filled with a non-solubilizing fluid, for example, an alcohol or an oil, with or without temperature control. Although not necessary, the cooled product may be further processed by size reduction, for example by knife cutting at the die, grinding, milling or pulverizing. The product may also be treated with an anti-caking compound either before or after size reduction.

In the extrusion process, the matrix mixture contains lower molecular weight components. For the composition containing hydrolyzed gelatin, polyols are preferred to avoid the Maillard browning reactions which result from the reaction of the side chain amino acids and reducing sugars. For the non-protein food polymers, the choice of low molecular weight carbohydrate is determined by the melt dynamics of the extruder. In certain cases, the monosaccharides and disaccharides can be in the form of hydrate crystals. For glucose monohydrate, the water contribution is 10% by weight of the crystalline sugar. For maltose or lactose monohydrate, that contribution falls to 5 wt. % added water. In such cases, the water stream added as a plasticizer for the melt will be adjusted to compensate for the internal free water contributed by the "melting" of the water of crystallization.

Other features of the invention will become apparent in the course of the following descriptions of exemplary embodiments which are given for illustration of the invention and are not intended to be limiting thereof.

EXAMPLES

Examples 1-6 and 8-11 and Comparative Example 7

Materials and Methods

Melt extrusion was accomplished utilizing a pilot plant 2" co-rotating twin-screw extruder incorporating oil jacket heating, fitted with a liquid injection port in the feeding zone of the unit, and utilizing a 0.036", a 0.046", or a 0.086" multi-orifice die. A matrix composition consisting of pre-blended food polymer(s), spices, herbs and low molecular weight carbohydrates was metered into the feed port at a feed rate between 100 to 200 g/min of solids; the water (plasticizer) liquid stream was delivered to the feed port by a metering peristaltic pump at approximately 2-12 g/min. The jacket temperature was set at 250° F. Liquid, oil soluble flavors or oils were used. In some cases, an emulsifier, such as Polysorbate 60 (polyoxyethylene [20] sorbitan monostearate), was added to the flavor at 0.5 to 5% (w/w emulsifier/flavor). After lining out the feed and conveying rates and bringing the unit into a steady-state, the extrudate was air cooled and collected in the form of fine strands which rapidly set into a brittle, glassy solid.

The setting time of the extruded strands was evaluated as a minimum time needed for the strands to reach a brittle breaking point. The particle density of milled extruded strands was measured with a Micromeritics powder pycnometer, model AccuRys 1330 (Micromeritics, Norcross, Ga. 30093) using helium as a filling gas.

A TA Instruments Modulated Differential Scanning calorimeter (MDSC) (TA Instruments, New Castle, Del. 19720) equipped with a DSC 2920 cell and a Refrigerated Cooling Unit was used to determine the glass transition temperature. Samples (up to 15 mg) were hermetically sealed in coated aluminum pans, and nitrogen was used as a purge gas. A modulated mode employed a sinusoidal modulation of linearly increasing temperature was used and allowed separation and characterization of glass transition as a reversing process. A heating ramp rate of 5° C./min was employed in the range from −12° C. to 90° C. in combination with +/−1° C. modulation amplitude and 30 sec period of modulation. Glass transition temperature was determined as a midpoint of the glass transition temperature interval. The MDSC tests were run in duplicate.

Example 1

A matrix composition consisting of 47.93% by weight of OSAN-starch (Emcap 12634, Cargill), 20% of ground oregano, 27.97% of lactose, 4.0% of dextrose monohydrate, and 0.1% of a powdered licorice extract was dry blended and fed at a rate of 114 g/min into the extruder. Deionized water was metered into the feed port at 3 g/min. The extruder jacket temperature was maintained at 250° F. A flavor containing by weight 40% of butter oil, 37.4% of sunflower oil, 14% of glycerol monooleate, 6% of glycerol lactopalmitate, 2.5% of vanilla extract, and 0.1% of hazelnut flavor was metered into the mix at 7.8 g/min. The encapsulate composition was extruded through a 0.036" multi-orifice die without puffing and the resulting solid was cooled by a cold airflow to yield a brittle solid in approximately 2 to 3 seconds. The resultant solid was characterized by MDSC (modulating differential scanning calorimetry) as a glass, with a glass transition temperature (Tg) of 44.9° C. The product had 7.6% moisture as determined by Karl Fisher analysis and 1.443 g/cc true specific gravity of the glassy particles as determined by a helium pycnometer.

Example 2

A matrix composition consisting of 59.9% by weight of maltodextrin 10 DE, 20% of ground oregano, 10% of beta-cyclodextrin, 10% of dextrose monohydrate, and 0.1% of a powdered licorice extract was dry blended and fed at a rate of 114 g/min into the extruder. Deionized water was metered into the feed port at 3 g/min. The extruder jacket temperature was maintained at 250° F. Sunflower oil was metered into the mix at 7.2 g/min. The encapsulate composition was extruded through a 0.036" multi-orifice die without puffing and the resulting solid was cooled by a cold airflow to yield a brittle solid in approximately 2 seconds. The resultant solid was characterized by MDSC (modulating differential scanning calorimetry) as a glass, with a glass transition temperature (Tg) of 54.7° C. The product had 6.8% moisture as determined by Karl Fisher analysis and 1.445 g/cc true specific gravity of the glassy particles as determined by a helium pycnometer.

Example 3

A matrix composition consisting of 80% by weight of maltodextrin 10 DE and 20% of a red pepper powder was dry blended and fed at a rate of 114 g/min into the extruder. Red pepper powder contained by weight 17.27% of total lipids and 10.34% of total sugars. Deionized water was metered into the feed port at 10 g/min. The extruder jacket temperature was maintained at 250° F. Sunflower oil was metered into the mix at 6.4 g/min. The encapsulate composition was extruded through a 0.086" multi-orifice die without puffing and the resulting solid was cooled by a cold airflow to yield a brittle solid in approximately 15 seconds. The resultant solid was characterized by MDSC (modulating differential scanning calorimetry) as a glass, with a glass transition temperature (Tg) of 48.9° C. The product had 8.2% moisture as determined by Karl Fisher analysis and 1.423 g/cc true specific gravity of the glassy particles as determined by a helium pycnometer.

Example 4

A matrix composition consisting of 71.95% by weight of larch gum, 20% of ground oregano, 8% of dextrose monohydrate, and 0.05% of a powdered licorice extract was dry blended and fed at a rate of 114 g/min into the extruder. Deionized water was metered into the feed port at 3.5 g/min. The extruder jacket temperature was maintained at 250° F. A flavor containing by weight 40% of butter oil, 37.5% of sunflower oil, 20% of glycerol monooleate, and 2.5% of a vanilla extract was metered into the mix at 8.7 g/min. The encapsulate composition was extruded through a 0.036" multi-orifice die without puffing and the resulting solid was cooled by a cold airflow to yield a brittle solid in approximately 3 seconds. The resultant solid was characterized by MDSC (modulating differential scanning calorimetry) as a glass, with a glass transition temperature (Tg) of 36.6° C. The product had 7.4% moisture as determined by Karl Fisher analysis and 1.453 g/cc true specific gravity of the glassy particles as determined by a helium pycnometer.

Example 5

A matrix composition consisting of 80% by weight of larch gum, 10% of fine grind black pepper, and 10% of dextrose monohydrate, was dry blended and fed at a rate of 114 g/min into the extruder. Deionized water was metered into the feed port at 4 g/min. The extruder jacket temperature was maintained at 250° F. A flavor containing by weight 23.75% of an oleo capsicum, 71.25% of fractionated coconut oil, and 5% of Polysorbate 60 was metered into the mix at 10.3 g/min. The encapsulate composition was extruded through a 0.036" multi-orifice die without puffing and the resulting solid was cooled by a cold airflow to yield a brittle solid in approximately 3 seconds. The resultant solid was characterized by MDSC (modulating differential scanning calorimetry) as a glass, with a glass transition temperature (Tg) of 33.6° C. The product had 7.2% moisture as determined by Karl Fisher analysis and 1.474 g/cc true specific gravity of the glassy particles as determined by a helium pycnometer.

Example 6

A matrix composition consisting of 70% by weight of gum Arabic, 20% of a red pepper powder, and 10% dextrose monohydrate was dry blended and fed at a rate of 114 g/min into the extruder. Red pepper powder contained by weight 17.27% of total lipids and 10.34% of total sugars. Deionized water was metered into the feed port at 8 g/min. The extruder jacket temperature was maintained at 250° F. Sunflower oil was metered into the mix at 6.5 g/min. The encapsulate composition was extruded through a 0.086" multi-orifice die with slight expansion and puffing and the resulting solid was cooled by a cold airflow to yield a brittle solid in approximately 15 seconds. The resultant solid was brittle and glassy at room temperature. The product had 6.9% moisture as determined by Karl Fisher analysis and 1.429 g/cc true specific gravity of the glassy particles as determined by a helium pycnometer.

Comparative Example 7

A matrix composition consisting of 80% by weight of maltodextrin 10 DE, and 20% of a turmeric powder was dry blended and fed at a rate of 114 g/min into the extruder. The turmeric powder contained by weight 9.88% of total lipids, 3.21% of total sugars, and 11.4% moisture. Deionized water was metered into the feed port at 11 g/min. The extruder jacket temperature was maintained at 250° F. Sunflower oil was metered into the mix at 6.4 g/min. The encapsulate composition was extruded through a 0.086" multi-orifice die without puffing and the resulting solid was cooled by a cold airflow to yield a solid in approximately 15 seconds. The resultant solid was not immediately brittle and glassy at room temperature. The product had 10.5% moisture as determined by Karl Fisher analysis and 1.453 g/cc true specific gravity of the particles as determined by a helium pycnometer. The process was not stable as the melt was constantly backing up into the feed zone. Total moisture content above 10% by weight of the composition prevented the process from being stable by the virtue of turmeric hydration and blocking the die with a high viscosity melt. Extrusion of the maltodextrin carrier was found especially sensitive to hydrated spices as maltodextrin does not have surface active properties and therefore does not emulsify efficiently oil soluble flavors or oils. Reducing water flow down to 9 g/min still did not help in stabilizing the process.

Example 8

A matrix composition consisting of 40% by weight of gum Arabic, 20% of finely ground oregano, 30% lactose, and 10% dextrose monohydrate was dry blended and fed at a rate of 114 g/min into the extruder. Deionized water was metered into the feed port at 2 g/min. The extruder jacket temperature was maintained at 250° F. Sunflower oil containing 5% by weight of decaglycerol monooleate was metered into the mix at 6.5 g/min. The encapsulate composition was extruded through a 0.046" multi-orifice die without expansion and the resulting solid was cooled by a cold airflow to yield a brittle solid in approximately 3 seconds. The resultant solid was characterized by MDSC (modulating differential scanning calorimetry) as a glass, with a glass transition temperature (Tg) of 35.3° C. The product had 7.5% moisture as determined by Karl Fisher analysis and 1.449 g/cc true specific gravity of the glassy particles as determined by a helium pycnometer.

Example 9

A matrix composition consisting of 70% by weight of hydrolyzed gelatin type B, 20% of finely ground oregano, and 10% mannitol was dry blended and fed at a rate of 114 g/min into the extruder. Deionized water was metered into the feed port at 3 g/min. The extruder jacket temperature was maintained at 250° F. Sunflower oil containing 5% by weight of decaglycerol monooleate was metered into the mix at 6.3 g/min. The encapsulate composition was extruded through a 0.046" multi-orifice die without expansion and the resulting solid was cooled by a cold airflow to yield a brittle solid in approximately 3 seconds. The resultant solid was characterized by MDSC (modulating differential scanning calorimetry) as a glass, with a glass transition temperature (Tg) of 41.1° C. The product had 9.9% moisture as determined by Karl Fisher analysis and 1.333 g/cc true specific gravity of the glassy particles as determined by a helium pycnometer.

Example 10

A matrix composition consisting of 50% by weight of polydextrose, 40% of black pepper fines (McCormick product code 774386), and 10% corn syrup solids 42DE was dry blended and fed at a rate of 200 g/min into the extruder. Deionized water was metered into the feed port at 2 g/min. The extruder jacket temperature was maintained at 250° F. Fractionated coconut oil containing 5% by weight of Polysorbate 60 (emulsifier) was metered into the mix at 5.3 g/min. The encapsulate composition was extruded through a 0.086" multi-orifice die without expansion and the resulting solid was cooled by a cold airflow to yield a brittle solid in approximately 3 seconds. The resultant solid was characterized by MDSC (modulating differential scanning calorimetry) as a glass, with a glass transition temperature (Tg) of 35.8° C. The product had water activity 0.425 measured at 21.7° C. and 1.429 g/cc true specific gravity of the glassy particles as determined by a helium pycnometer.

Example 11

A matrix composition consisting of 39% by weight of inulin, 10% gum Arabic, 40% of black pepper fines (McCormick product code 774386) and 11% corn syrup solids 42DE was dry blended and fed at a rate of 200 g/min into the extruder. Deionized water was metered into the feed port at 3 g/min. The extruder jacket temperature was maintained at 250° F. High oleic sunflower oil (Trisun 80) containing 5% by weight of sunflower lecithin (Giralec Premium) was metered into the mix at 5.1 g/min. The encapsulate composition was extruded through a 0.086" multi-orifice die without expansion and the resulting solid was cooled by a cold airflow to yield a brittle solid in approximately 15 seconds. The resultant solid was characterized by MDSC (modulating differential scanning calorimetry) as a glass, with a glass transition temperature (Tg) of 42.2° C.

Where a numerical limit or range is stated herein, the endpoints are included. Also, all values and sub ranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. An extrusion encapsulation composition, comprising:
(A) an encapsulate, encapsulated in (B) a glassy matrix, wherein:
said glassy matrix (B) is a composition, comprising: 5 to 40% by weight, based on the total weight of said matrix (B), of at least one spice or herb; 5 to 40% by weight, based on the total weight of said matrix (B), of at least one component selected from the group consisting of a low molecular weight sugar, a low molecular weight polyol, and a corn syrup solid; and 40 to 90% by weight, based on the total weight of said matrix (B), of at least one component selected from the group consisting of an n-octenylsuccinic acid anhydride-modified starch, maltodextrin, larch gum, gum Arabic, inulin, cyclodextrin, polydextrose, and hydrolyzed gelatin,
wherein said extrusion encapsulation composition is prepared by a process comprising:
(i) blending the components of said matrix composition (B) as a dry powder;
(ii) mixing the dry blend of said components of said matrix composition (B) with water as a plasticizer and said encapsulate (A) in an extruder, to obtain a melted mixture comprising said encapsulate (A) and said components of said matrix composition (B); and
(iii) extruding said melted mixture, to obtain said extrusion encapsulation composition, wherein said encapsulate (A) is encapsulated in a glassy matrix of said matrix composition (B), and
said extrusion encapsulation composition comprises less than 10% water and an encapsulate (A) in the range from 0.1% to 20% by weight, based on the total weight of the extrusion encapsulation composition.

2. A composition according to claim 1, which has a glass transition temperature of 30° C. to 55° C.

3. A composition according to claim 1, wherein said matrix (B) comprises 10% to 30% by weight, based on the total weight of said composition (B), of at least one spice or herb.

4. A composition according to claim 1, wherein said encapsulate is selected from the group consisting of a medication, a pesticide, a vitamin, a preservative, and a flavor.

5. A composition according to claim 4, wherein said encapsulate is a flavor.

6. A composition according to claim 5, wherein said flavor is selected from the group consisting of a natural extract, an oleoresin, an essential oil, a protein hydrolyzate, an aqueous reaction flavor, and a compounded flavor.

7. A composition according to claim 1, wherein said matrix (B) comprises 10 to 30% by weight, based on the total weight of said matrix (B), of at least one spice or herb; 10 to 30% by weight, based on the total weight of said matrix (B), of at least one component selected from the group consisting of a low molecular weight sugar, a low molecular weight polyol, and a corn syrup solid; and 60 to 80% by weight, based on the total weight of said matrix (B), of at least one component selected from the group consisting of an n-octenylsuccinic acid anhydride-modified starch, maltodextrin, larch gum, gum Arabic, inulin, cyclodextrin, polydextrose, and hydrolyzed gelatin.

8. A composition according to claim 1, wherein said matrix (B) is a composition comprising 15 to 25% by weight, based on the total weight of said matrix (B), of at least one spice or herb; 10 to 30% by weight, based on the total weight of said matrix (B), of at least one component selected from the group consisting of a low molecular weight sugar, a low molecular weight polyol, and a corn syrup solid; and 60 to 70% by weight, based on the total weight of said matrix (B), of at least one component selected from the group consisting of an n-octenylsuccinic acid anhydride-modified starch, maltodextrin, larch gum, gum Arabic, inulin, cyclodextrin, polydextrose, and hydrolyzed gelatin.

9. A method of making an extrusion encapsulation composition, comprising:
(A) an encapsulate, encapsulated in (B) a glassy matrix, wherein:
said glassy matrix (B) is a composition, comprising: 5 to 40% by weight, based on the total weight of said matrix (B), of at least one spice or herb; 5 to 40% by weight, based on the total weight of said matrix (B), of at least one component selected from the group consisting of a low molecular weight sugar, a low molecular weight polyol, and a corn syrup solid; and 40 to 90% by weight, based on the total weight of said matrix (B), of at least one component selected from the group consisting of an n-octenylsuccinic acid anhydride-modified starch, maltodextrin, larch gum, gum Arabic, inulin, cyclodextrin, polydextrose, and hydrolyzed gelatin,
said extrusion encapsulation composition contains less than 10% water and an encapsulate (A) in the range from 0.1% to 20% by weight, based on the total weight of the extrusion encapsulation composition,
said method comprising:
(i) blending the components of said matrix composition (B) as a dry powder;
(ii) mixing the dry blend of said components of said matrix composition (B) with water as a plasticizer and said encapsulate (A) in an extruder, to obtain a melted mixture comprising said encapsulate (A) and said components of said matrix composition (B); and
(iii) extruding said melted mixture, to obtain said composition, wherein said encapsulate (A) is encapsulated in a glassy matrix of said matrix composition (B).

10. A method according to claim 9, wherein said extrusion encapsulation composition has a glass transition temperature of 30° C. to 55° C.

11. A method according to claim 9, wherein said matrix (B) comprises 10% to 30% by weight, based on the total weight of said composition (B), of at least one spice or herb.

12. A method according to claim 9, wherein said encapsulate is selected from the group consisting of a medication, a pesticide, a vitamin, a preservative, and a flavor.

13. A method according to claim 12, wherein said encapsulate is a flavor.

14. A method according to claim 13, wherein said flavoring agent is selected from the group consisting of a natural extract, an oleoresin, an essential oil, a protein hydrolyzate, an aqueous reaction flavor, and a compounded flavor.

15. A method according to claim 9, wherein said matrix (B) is a composition comprising 10 to 30% by weight, based on the total weight of said matrix (B), of at least one spice or herb; 10 to 30% by weight, based on the total weight of said matrix (B), of at least one component selected from the group consisting of a low molecular weight sugar, a low molecular weight polyol, and a corn syrup solid; and 60 to 80% by weight, based on the total weight of said matrix (B), of at least one component selected from the group consisting of an n-octenylsuccinic acid anhydride-modified starch, maltodextrin, larch gum, gum Arabic, inulin, cyclodextrin, polydextrose, and hydrolyzed gelatin.

16. A method according to claim 9, wherein said matrix (B) is a composition comprising 15 to 25% by weight, based on the total weight of said matrix (B), of at least one spice or herb; 10 to 30% by weight, based on the total weight of said matrix (B), of at least one component selected from the group consisting of a low molecular weight sugar, a low molecular weight polyol, and a corn syrup solid; and 60 to 70% by weight, based on the total weight of said matrix (B), of at least one component selected from the group consisting of an n-octenylsuccinic acid anhydride-modified starch, maltodextrin, larch gum, gum Arabic, inulin, cyclodextrin, polydextrose, and hydrolyzed gelatin.

17. A composition according to claim 1, wherein said matrix (B) comprises 20% to 40% by weight, based on the total weight of said composition (B), of at least one spice or herb.

18. A composition according to claim 1, wherein said spice or herb is one more spice or herb selected from the group consisting of ajowan, alexanders, allspice, almond, aloe, angelica, anise, anise-pepper, annatto, areca nut, asafoetida, avens, balm, sweet basil, bay, bergamot, borage, calamint, chamomile, candlenut, caper, caraway, cardamom, catmint, celery, garden chervil, chicory, chive, cinnamon, cassia, citron, clary, clove, coconut, coffee, cola, coriander, costmary, cress, cumin, curry leaf, dill, fennel, fenugreek, galangal, garlic, garlic mustard, ginger, grains of paradise, hop, hyssop, juniper, leek, lemon grass, liquorice, lovage, mace, malt, marjoram, mint, dried edible mushrooms, mustard, nutmeg, onion, oregano, parsley, pepper, poppy, rosemary, saffron, sage, samphire, sesame, star anise, tarragon, thyme, turmeric, and vanilla.

19. A composition according to claim 1, wherein said spice or herb has a size of from 20 microns to about 2 millimeters.

20. A composition according to claim 1, wherein:
said matrix (B) comprises 20% to 40% by weight, based on the total weight of said composition (B), of at least one spice or herb;
spice or herb is one more spice or herb selected from the group consisting of ajowan, alexanders, allspice, almond, aloe, angelica, anise, anise-pepper, annatto, areca nut, asafoetida, avens, balm, sweet basil, bay, bergamot, borage, calamint, chamomile, candlenut, caper, caraway, cardamom, catmint, celery, garden chervil, chicory, chive, cinnamon, cassia, citron, clary, clove, coconut, coffee, cola, coriander, costmary, cress, cumin, curry leaf, dill, fennel, fenugreek, galangal, garlic, garlic mustard, ginger, grains of paradise, hop, hyssop, juniper, leek, lemon grass, liquorice, lovage, mace, malt, marjoram, mint, dried edible mushrooms, mustard, nutmeg, onion, oregano, parsley, pepper, poppy, rosemary, saffron, sage, samphire, sesame, star anise, tarragon, thyme, turmeric, and vanilla; and
said spice or herb has a size of from 20 microns to about 2 millimeters.

21. A method according to claim 9, wherein said matrix (B) comprises 20% to 40% by weight, based on the total weight of said composition (B), of at least one spice or herb.

22. A method according to claim 9, wherein said spice or herb is one more spice or herb selected from the group consisting of ajowan, alexanders, allspice, almond, aloe, angelica, anise, anise-pepper, annatto, areca nut, asafoetida, avens, balm, sweet basil, bay, bergamot, borage, calamint, chamomile, candlenut, caper, caraway, cardamom, catmint, celery, garden chervil, chicory, chive, cinnamon, cassia, citron, clary, clove, coconut, coffee, cola, coriander, costmary, cress, cumin, curry leaf, dill, fennel, fenugreek, galangal, garlic, garlic mustard, ginger, grains of paradise, hop, hyssop, juniper, leek, lemon grass, liquorice, lovage, mace, malt, marjoram, mint, dried edible mushrooms, mustard, nutmeg, onion, oregano, parsley, pepper, poppy, rosemary, saffron, sage, samphire, sesame, star anise, tarragon, thyme, turmeric, and vanilla.

23. A method according to claim 9, wherein said spice or herb has a size of from 20 microns to about 2 millimeters.

24. A method according to claim 9, wherein:
said matrix (B) comprises 20% to 40% by weight, based on the total weight of said composition (B), of at least one spice or herb;
said spice or herb is one more spice or herb selected from the group consisting of ajowan, alexanders, allspice, almond, aloe, angelica, anise, anise-pepper, annatto, areca nut, asafoetida, avens, balm, sweet basil, bay, bergamot, borage, calamint, chamomile, candlenut, caper, caraway, cardamom, catmint, celery, garden chervil, chicory, chive, cinnamon, cassia, citron, clary, clove, coconut, coffee, cola, coriander, costmary, cress, cumin, curry leaf, dill, fennel, fenugreek, galangal, garlic, garlic mustard, ginger, grains of paradise, hop, hyssop, juniper, leek, lemon grass, liquorice, lovage, mace, malt, marjoram, mint, dried edible mushrooms, mustard, nutmeg, onion, oregano, parsley, pepper, poppy, rosemary, saffron, sage, samphire, sesame, star anise, tarragon, thyme, turmeric, and vanilla; and
said spice or herb has a size of from 20 microns to about 2 millimeters.

25. A composition according to claim 1, which comprises less than 9% water.

26. A composition according to claim 1, which comprises less than 8% water.

27. A composition according to claim 1, which comprises 2 to 9% water.

28. A composition according to claim 1, which comprises 3 to 8% water.

29. A composition according to claim 1, wherein said melted mixture is extruded through a die and said extrusion encapsulation composition is capable of being cut at said die or milled after cooling.

30. A method according to claim 9, wherein said extrusion encapsulation composition comprises less than 9% water.

31. A method according to claim 9, wherein said extrusion encapsulation composition comprises less than 8% water.

32. A method according to claim 9, wherein said extrusion encapsulation composition comprises 2 to 9% water.

33. A method according to claim 9, wherein said extrusion encapsulation composition comprises 3 to 8% water.

34. A method according to claim 9, wherein said melted mixture is extruded through a die and said extrusion encapsulation composition is capable of being cut at said die or milled after cooling.

* * * * *